US006420108B2

United States Patent
Mack et al.

(10) Patent No.: US 6,420,108 B2
(45) Date of Patent: *Jul. 16, 2002

(54) COMPUTER-AIDED DISPLAY FOR COMPARATIVE GENE EXPRESSION

(75) Inventors: David H. Mack, Menlo Park; Elina Khurgin, Cupertino; Josie Dai, San Jose; Kurt Gish, Sunnyvale; Jim Snyder, Palo Alto; David Balaban, San Jose, all of CA (US)

(73) Assignee: Affymetrix, Inc., Santa Clara, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/020,743

(22) Filed: Feb. 9, 1998

(51) Int. Cl.[7] .......................... C12Q 1/68; G01N 33/53; G01N 33/48; C07H 21/04
(52) U.S. Cl. .......................... 435/6; 435/7.1; 536/24.3; 536/24.31; 536/24.33; 702/19; 702/20
(58) Field of Search ..................... 435/6, 7.1; 536/24.3, 536/24.31, 24.33; 702/19, 20

(56) References Cited

U.S. PATENT DOCUMENTS

| | | | |
|---|---|---|---|
| 4,683,202 A | 7/1987 | Mullis | |
| 5,143,854 A | 9/1992 | Pirrung et al. | 436/518 |
| 5,206,137 A | 4/1993 | Ip et al. | |
| 5,445,934 A | 8/1995 | Fodor et al. | 435/6 |

(List continued on next page.)

FOREIGN PATENT DOCUMENTS

| | | | |
|---|---|---|---|
| EP | 0 307 476 A1 | 3/1989 | C07K/15/12 |
| EP | 0 235 726 | 5/1989 | |
| EP | 0 392 546 A2 | 10/1990 | C12Q/1/68 |
| EP | 0 717 113 | 7/1996 | |

(List continued on next page.)

OTHER PUBLICATIONS

Zhao et al Gene vol. 156 pp. 207–213, 1995.*
Guo et al NAR vol. 22 (24) pp. 5456–5465, 1994.*
U.S. application No. 08/828,952, Webster et al., filed Mar. 28, 1997.
Drmanac, "Sequencing Of Megabase Plus DNA By Hybridization: Theory Of The Method," *Genomics*, 4:114–128 (1989).
Adams et al., "Complementary DNA Sequencing: Expressed Sequence Tags and Human Genome Project", *Science*, 252(5013):1651–1656 (1991).
Frickett et al., "Development Of A Database For Nucleotide Sequences", *Mathematical Methods for DNA Sequences*, CRC Press, Ed. Waterman, pp. 2–34 (1989).
Hara et al., "Subtractive cDNA Cloning Using Oligo $(dT)_{30}$–Latex And PCR: Isolation Of cDNA Clones Specific To Undifferentiated Human Embryonal Carcinoma Cells", *Nucleic Acids Res.*, 19(25):7097–7104 (1991).

(List continued on next page.)

*Primary Examiner*—Jeffrey Siew
(74) *Attorney, Agent, or Firm*—Townsend and Townsend and Crew LLP

(57) ABSTRACT

Innovative systems and methods for visualizing information collected from analyzing samples are provided. The samples may include nucleic acids, proteins, or other polymers. Gene expression level as determined from analysis of a nucleic acid sample is one possible analysis result that may be visualized. In one embodiment, a computer system may display the expression levels of multiple genes simultaneously in a way that facilitates user identification of genes whose expression is significant to a characteristic such as disease or resistance to disease. Additionally, the computer system may facilitate display of further information about relevant genes once they are identified.

50 Claims, 6 Drawing Sheets

U.S. PATENT DOCUMENTS

| | | | |
|---|---|---|---|
| 5,492,806 A | 2/1996 | Drmanac et al. | 435/6 |
| 5,525,464 A | 6/1996 | Drmanac et al. | 435/6 |
| 5,571,639 A | 11/1996 | Hubbell et al. | 430/5 |
| 5,593,839 A | 1/1997 | Hubbell et al. | 435/6 |
| 5,667,972 A | 9/1997 | Drmanac et al. | 435/6 |
| 5,695,940 A | 12/1997 | Drmanac et al. | 435/6 |
| 5,700,637 A | 12/1997 | Southern | 435/6 |
| 5,707,806 A | 1/1998 | Shuber | |
| 5,777,888 A | 7/1998 | Rine et al. | 364/496 |
| 5,843,767 A * | 12/1998 | Beattie | |
| 5,871,697 A | 2/1999 | Rothberg et al. | |
| 6,023,659 A * | 2/2000 | Seihamer et al. | |
| 6,028,593 A * | 2/2000 | Rosenberg et al. | |

FOREIGN PATENT DOCUMENTS

| | | | |
|---|---|---|---|
| EP | 0 848 067 | 6/1998 | |
| EP | 0848067 A2 * | 6/1998 | |
| WO | WO 89/11548 | 11/1989 | |
| WO | WO 90/15070 | 12/1990 | C07K/1/04 |
| WO | WO 92/10092 | 6/1992 | A01N/1/02 |
| WO | WO 92/10588 | 6/1992 | C12Q/1/68 |
| WO | WO 93/22456 | 11/1993 | |
| WO | WO 95/11995 | 5/1995 | C12Q/1/68 |
| WO | WO 96/23078 | 8/1996 | |
| WO | WO 97/10365 | 3/1997 | C12Q/1/68 |
| WO | WO 97/17317 | 5/1997 | C07C/59/90 |
| WO | WO 97/19410 | 5/1997 | G06F/13/364 |
| WO | WO 97/27317 | 7/1997 | C12Q/1/68 |
| WO | WO 97/29212 | 8/1997 | C12Q/1/68 |

OTHER PUBLICATIONS

Khan et al., "Single Pass Sequencing And Physical And Genetic Mapping Of Human Brain cDNAs", *Nat Genet.*, 2(3):180–185 (1992).

Matsubara et al., "Identification Of New Genes By Systematic Analysis Of cDNAs And Database Contruction", *Curr. Opin. Biotechnol.*, 4(6) 1993).

U.S. application No. 08/531,137, Chen et al., filed Oct. 16, 1995.

Gibbs et al., "Detection of Single DNA Base Differences by Competitive Oligonucleotide Priming", *Nucleic Acid Res.*, 17(7):2437–2448 (1989).

Guatelli et al., "Isothermal, In Vitro Amplification of Nucleic Acids by Multienzyme Reaction Modeled After Retroviral Replication", *Proc. Natl. Acad. Sci. USA*, 87(5):1874–1878 (1990).

Gusella, "DNA Polymorphism and Human Disease", *Annu. Rev. Biochem.*, 55:831–854 (1986).

Intelligenectics Suite (TM), Release 5.4, Advanced Training Manual, Jan. 1993, published by IntelliGenetics, Inc., 700 East El Camino Real, Mountain View, California 94040, USA, pp. (1–6) –(1–19) and (2–9) –(2–14), see entire document.

Kwob et al., "Transcription–Based Amplification System and Detection of Amplified Human Immunodeficiency Virus Type 1 With a Bead–Based Sandwich Hybridization Format", *Proc. Natl. Acad. Sci. USA*, 86(4):1173–1177 (1989).

Landegren et al., "A Ligase–Mediated Gene Detection Technique", *Science*, 241(4869):1077–1080 (1988).

Mattila et al., "Fidelity of DNA Synthesis by the *Thermoccus litoralis* DNA Polymerase—An Extremely Heat Stable Enzyme With Proofreading Activity", *Nucleic Acids Res.*, 19(18):4967–4973 (1991).

Okubo et al., "Large Scale cDNA Sequencing for Analysis of Quantitative and Qualitative Aspects of Gene Expression", *Nature Genetics*, 2(3):173–179 (1993).

Orita et al., "Detection of Polymorphisms of Human DNA by Gel Electrophoresis as Single–Strand Conformation Polymorphisms", *Proc. Natl. Acad. Sci. USA*, 86(8):2766–2770 (1989).

Saiki et al., "Analysis of Enzymatically Amplified Beta- -Globin and HLA–DQ Alpha DNA with Allele–Specific Oligonucleotide Probes", *Nature*, 324(6093):163–166 (1986).

Wu et al., "The Ligation Amplification Reaction (LAR)— Amplification of Specific DNA Sequences Using Sequential Rounds of Template–Dependent Ligation", *Genomics*, 4(4):560–569 (1989).

PR Newswire, "Gen Logic to Use Affymetrix GeneChip Arrays to Build Gene Expression Database Products", Jan. 11, 1999.

* cited by examiner

| CLUSTER | ACCESSION NUMBER | DESCRIPTION |
|---|---|---|
| Hsa.35 | D11327 | Human mRNA for protein-tyrosine phosphatase; complete cds. |
| 702 | 704 | 706 |

```
LOCUS       HUMLCPTP      2691 bp    mRNA            PRI        06-NOV-1992
DEFINITION  Human mRNA for protein-tyrosine phosphatase, complete cds.
ACCESSION   D11327
NID         g219901
KEYWORDS    protein-tyrosine phosphatase.
SOURCE      Human T cell, lambda-gt10 library, cDNA to mRNA.
  ORGANISM  Homo sapiens
            Eukaryotae; mitochondrial eukaryotes; Metazoa; Chordata;
            Vertebrata; Mammalia; Eutheria; Primates; Catarrhini; Hominidae;
            Homo.
REFERENCE   1  (bases 1 to 2691)
  AUTHORS   Adachi,T., Sekiya,M., Isobe,M., Kumura,Y., Ogita,Z., Hinoda,Y.,
            Imai,K. and Yachi,A.
  TITLE     Molecular cloning and chromosomal mapping of a human
            protein-tyrosine phosphatase LC-PTP
  JOURNAL   Biochemical and Biophysical Research Communication 186, 1607-1615
            (1992)
COMMENT     Submitted (22-MAY-1992) to DDBJ by:
            Masaaki Adachi
            Sapporo Medical College
            S1W16 Chuo-ku
            Sapporo 060
            Japan
            Phone:   011-611-2111
            Fax:     011-613-1141.
FEATURES             Location/Qualifiers
     source          1..2691
                     /organism="Homo sapiens"
                     /db_xref="taxon:9606"
                     /cell_type="T cell"
                     /clone_lib="lambda-gt10"
     gene            105..1187
                     /gene="LC-PTP"
     CDS             105..1187
                     /gene="LC-PTP"
                     /codon_start=1
                     /product="protein-tyrosine phosphatase"
                     /db_xref="PID:d1002425"
                     /db_xref="PID:g219902"
                     /translation="MVQAHGGRSRAQPLTLSLGAAMTQPPPEKTPAKKHVRLQERRGS
                     NVALMLDVRSLGAVEPICSVNTPREVTLHFLRTAGHPLTRWALQRQPPSPKQLEEEFL
                     KIPSNFVSPEDLDIPGHASKDRYKTILPNPQSRVCLGRAQSQEDGDYINANYIRGYDG
                     KEKVYIATQGPMPNTVSDFWEMVWQEEVSLIVMLTQLREGKEKCVHYWPTEEETYGPF
                     QIRIQDMKECPEYTVRQLTIQYQEERRSVKHILFSAWPDHQTPESAGPLLRLVAEVEE
                     SPETAAHPGPIVVHCSAGIGRTGCFIATRIGCQQLKARGEVDILGIVCQLRLDRGGMI
                     QTDEQYQFLHHTLALYAGQLPEEPSP"
     misc_feature    444..1172
                     /gene="LC-PTP"
                     /note="single catalytic domain"
     polyA_signal    2667..2672
     polyA_site      2691
BASE COUNT      652 a    816 c    707 g    516 t
ORIGIN
        1 ggagacagac agacagctgg caagaggcag cctgggggcc acagctgctt cagcagacct
       61 catggctgag tgagcctccc ctgggccag cacccacct cagcatggtc caagcccatg
      121 gggggcgctc cagagcacag ccgttgacct tgtctttggg ggcagccatg acccagcctc
      181 cgcctgaaaa aacgccagcc aagaagacag tgccgctgca ggagaggcgg ggctccaatg
      241 tggctctgat gctggacgtt cggtccctga gggccgtaga acccatctgc tctgtgaaca
      301 caccccggga ggtcacccta cactttctgc gcactgctgg cacccccctt acccgctggg
      361 cccttcagcg ccagccaccc agccccaagc aactggaaga agaattcttg aagatccctt
      421 caaactttgt cagccccgaa gacctggaca tccctggcca cgcctccaag gaccgataca
      481 agaccatctt gccaaatccc cagagccgtg tctgtctagg ccgggcacag agccaggagg...
```

FIG. 7B

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
        (A) LENGTH: 2691 base pairs
        (B) TYPE: nucleic acid
        (C) STRANDEDNESS: unknown
        (D) TOPOLOGY: not relevant (ii) MOLECULE TYPE: DNA (genomic)

(vi) ORIGINAL SOURCE:
        (A) ORGANISM: Homo sapiens (xi) SEQUENCE DESCRIPTION: SEQ ID NO: 1:

GGAGACAGAC AGACAGCTGG CAAGAGGCAG CCTGGGGGCC ACAGCTGCTT CAGCAGACCT    60

```
CATGGCTGAG TGAGCCTCCC CTGGGCCCAG CACCCCACCT CAGCATGGTC CAAGCCCAT      120

GGGGGCGCTC CAGAGCACAG CCGTTGACCT TGTCTTTGGG GGCAGCCATG ACCCAGCCT      180

CGCCTGAAAA AACGCCAGCC AAGAAGCATG TGCGACTGCA GGAGAGGCGG GGCTCCAAT      240

TGGCTCTGAT GCTGGACGTT CGGTCCCTGG GGGCCGTAGA ACCCATCTGC TCTGTGAAC      300

CACCCCGGGA GGTCACCCTA CACTTTCTGC GCACTGCTGG ACACCCCTT ACCCGCTGG       360

CCCTTCAGCG CCAGCCACCC AGCCCCAAGC AACTGGAAGA AGAATTCTTG AAGATCCCT      420

CAAACTTTGT CAGCCCCGAA GACCTGGACA TCCCTGGCCA CGCCTCCAAG GACCGATAC      480

AGACCATCTT GCCAAATCCC CAGAGCCGTG TCTGTCTAGG CCGGGCACAG AGCCAGGAG      540

ACGGAGATTA CATCAATGCC AACTACATCC GAGGCTATGA CGGGAAGGAG AAGGTCTAC      600

TTGCCACCCA GGGCCCCATG CCCAACACTG TGTCGGACTT CTGGGAGATG GTGTGGCAA      660

AGGAAGTGTC CCTCATTGTC ATGCTCACTC AGCTCCGAGA GGGCAAGGAG AAATGTGTC      720

ACTACTGGCC CACAGAAGAG GAAACCTATG GACCCTTCCA GATCCGCATC CAGGACATG      780

AAGAGTGCCC AGAATACACT GTGCGGCAGC TCACCATCCA GTACCAGGAA GAGCGCCGG      840

CAGTAAAGCA CATCCTCTTT TCGGCCTGGC CAGACCATCA GACACCAGAA TCAGCTGGG      900

CCCTGCTGCG CCTAGTGGCA GAGGTGGAGG AGAGCCCGGA GACAGCCGCC CACCCCGGG      960

CTATCGTAGT CCACTGCAGT GCAGGGATTG GCCGGACGGG CTGCTTCATC GCCACGCG     1020

TTGGCTGTCA ACAGCTGAAA GCCCGAGGAG AAGTGGACAT TCTGGGTATT GTGTGCCA     1080

TGCGGCTAGA CAGAGGGGGG ATGATCCAGA CGGACGAGCA GTACCAGTTC CTGCACCA     1140

CTTTGGCCCT GTATGCAGGC CAGCTGCCTG AGGAACCCAG CCCCTGACCC CTGCCACC     1200

CCGGTGGCCC AGGTGCCTAC CTCCCTCAAG CCTGGGAAGT CACAGGAAGC AGCAGCAG     1260

AGGACAAGGG GCCGGATTCC AGGTCTTCAA CACTGGCCAC TCCTCTGCTT CCTCTGTT     1320

CCCCAGATGG ACAGTAAGGG GAACCTCCAA TGTCTCTCTG AACTTAAAGA CAGGAGCT     1380

CATTTATGAC AGACAAAGAA AGAAGCCCAG GTGTCCTGGT GTTCTCTGAG ACACTCTT     1440

TGAGCTTCAG TTTCCTGTTC TATAACATGA ACATAAGTGC TTAGCTGCCA TGAGGGAA     1500

GTAATGAGAG AAGTTTCTAG AAGCCACTCC AGCCACTCCT TCCTGGGGCT GACAAAAG     1560

TGATTCCAAG ATCATCCTTC ACCCGAGGTC CTGCCCAAGC ACAGGCCAGA TGCAAGAA     1620

GGGAAAAGTC TGGTCCTGAT CTCCAAGTCT CAACATCCTA TCAGTGACTC TGCTCCCT     1680

CCACACATCG GAAGGCTGG ATGACCCCAA TCAAAAGAAA GAACAAGGAC TCTGGTTA      1740

CTTGCCCTCC ACCCATGTGT CATAAGAGTA GGCTACAGAG GTGACCAGGC CTGGCAGT     1800

AAATCTCTGG AAGAGGGAAC ATGTGGGGAC TACTCAGAGG CAAAGAGGAG CTGCTCCT     1860

CTCCATGGTT GCTGGCCACT CCCACCAACT ACTCTTAGGG AGGCTAAGCA GTCTCTGT     1920

TGCTTCCATG GCTCAAATAA TACCCTGGGT ATGCAGGACC CACTATACCT TGCATTTG     1980

GGTACACCTA GAGAGCTTGG CTGTTTCCAA AAACAATCAG GGTCATAACC ATCCATGC     2040

ACATGGAGGC TCGGCTGAAC CAGGACTCCT CACTGTCTAC CTGAGAGAAT GAGCACCC     2100

CATCCATCTC AGCATCAACA CAATTTCCAG GGGACCTCAG GTCTACCTCA GGACTGAA     2160

CCACACCTCA GGATTCCTCC TCCTTGAATC TGAGACTGGC TGCCCATTCT GAGATGGG     2220

TGAAGGTAAG ATGCCGCATC ACCAGGCACG CCGCCCCTGA CAGCTGCCTT GATACCAG     2280

CTCTGTGGAA ACCCCGAGG AGTTGGATCT GGAGAACAGC TGGGCCTCCT CACTCAGG      2340

TTCTCTCCTG AAGAACACGC AGTGCTAAAA CTGAGGATGA TTTCCCTAAT GCTTCTGC     2400

GGCCTTATGG AGGAGCTGCT CCTTCCTTAC AGCCTTGGGG ATGGACTTGC CCACACCT     2460
```

-continued

```
ACCTCCCCTG AGCCCTGTGA GAGGCACGAC TGTCTATGCC AATGAGGCTC GGTGGGGG      2520

TCTCAAGTGC CTGATCCTGC CCTGGGCTCA GAGCCAGCCC AGAGGGAAGC AACTGCAC      2580

CCCCACAGGC CCTCCCTGGC ACTGTCCCCC CAACCCCATC TCAGAGCTCA GAGGGTAC      2640

GCTCCAGAAC AGTAACCAAG TGGGAAAATA AAGACTTCTT GGATGACTGA C             2691
```

(2) INFORMATION FOR SEQ ID NO: 2:

(i) SEQUENCE CHARACTERISTICS:
        (A) LENGTH: 360 amino acids
        (B) TYPE: amino acid
        (C) STRANDEDNESS: not relevant
        (D) TOPOLOGY: not relevant (ii) MOLECULE TYPE: protein (vi) ORIGINAL SOURCE:
        (A) ORGANISM: Homo sapiens (xi) SEQUENCE DESCRIPTION: SEQ ID NO: 2:

```
Met Val Gln Ala His Gly Gly Arg Ser Arg Ala Gln Pro Leu Thr Leu
1               5                  10                  15

Ser Leu Gly Ala Ala Met Thr Gln Pro Pro Glu Lys Thr Pro Ala
            20                  25                  30

Lys Lys His Val Arg Leu Gln Glu Arg Arg Gly Ser Asn Val Ala Leu
        35                  40                  45

Met Leu Asp Val Arg Ser Leu Gly Ala Val Glu Pro Ile Cys Ser Val
    50                  55                  60

Asn Thr Pro Arg Glu Val Thr Leu His Phe Leu Arg Thr Ala Gly His
65                  70                  75                  80

Pro Leu Thr Arg Trp Ala Leu Gln Arg Gln Pro Pro Ser Pro Lys Gln
                85                  90                  95

Leu Glu Glu Glu Phe Leu Lys Ile Pro Ser Asn Phe Val Ser Pro Glu
            100                 105                 110

Asp Leu Asp Ile Pro Gly His Ala Ser Lys Asp Arg Tyr Lys Thr Ile
        115                 120                 125

Leu Pro Asn Pro Gln Ser Arg Val Cys Leu Gly Arg Ala Gln Ser Gln
    130                 135                 140

Glu Asp Gly Asp Tyr Ile Asn Ala Asn Tyr Ile Arg Gly Tyr Asp Gly
145                 150                 155                 160

Lys Glu Lys Val Tyr Ile Ala Thr Gln Gly Pro Met Pro Asn Thr Val
                165                 170                 175

Ser Asp Phe Trp Glu Met Val Trp Gln Glu Val Ser Leu Ile Val
            180                 185                 190

Met Leu Thr Gln Leu Arg Glu Gly Lys Glu Lys Cys Val His Tyr Trp
        195                 200                 205

Pro Thr Glu Glu Glu Thr Tyr Gly Pro Phe Gln Ile Arg Ile Gln Asp
    210                 215                 220

Met Lys Glu Cys Pro Glu Tyr Thr Val Arg Gln Leu Thr Ile Gln Tyr
225                 230                 235                 240

Gln Glu Glu Arg Arg Ser Val Lys His Ile Leu Phe Ser Ala Trp Pro
                245                 250                 255

Asp His Gln Thr Pro Glu Ser Ala Gly Pro Leu Leu Arg Leu Val Ala
            260                 265                 270

Glu Val Glu Glu Ser Pro Glu Thr Ala Ala His Pro Gly Pro Ile Val
        275                 280                 285
```

```
                                -continued

Val His Cys Ser Ala Gly Ile Gly Arg Thr Gly Cys Phe Ile Ala Thr
    290                 295                 300

Arg Ile Gly Cys Gln Gln Leu Lys Ala Arg Gly Glu Val Asp Ile Leu
305                 310                 315                 320

Gly Ile Val Cys Gln Leu Arg Leu Asp Arg Gly Gly Met Ile Gln Thr
                325                 330                 335

Asp Glu Gln Tyr Gln Phe Leu His His Thr Leu Ala Leu Tyr Ala Gly
                340                 345                 350

Gln Leu Pro Glu Glu Pro Ser Pro
        355                 360
```

COMPUTER-AIDED DISPLAY FOR COMPARATIVE GENE EXPRESSION

BACKGROUND OF THE INVENTION

The present invention relates to the field of computer systems. More specifically, the present invention relates to computer systems for visualizing analysis results.

Devices and computer systems for forming and using arrays of materials on a substrate are known. For example, PCT Publication No. WO92/10588, incorporated herein by reference for all purposes, describes techniques for sequencing or sequence checking nucleic acids and other materials. Arrays for performing these operations may be formed according to the methods of, for example, the pioneering techniques disclosed in U.S. Pat. No. 5,143,854 and U.S. Pat. No. 5,593,839 both incorporated herein by reference for all purposes.

According to one aspect of the techniques described therein, an array of nucleic acid probes is fabricated at known locations on a substrate or chip. A fluorescently labeled nucleic acid is then brought into contact with the chip and a scanner generates an image file (which is processed into a cell file) indicating the locations where the labeled nucleic acids bound to the chip. Based upon the cell file and identities of the probes at specific locations, it becomes possible to extract information such as the monomer sequence of DNA or RNA. Such systems have been used to form, for example, arrays of DNA that may be used to study and detect mutations relevant to cystic fibrosis, the P53 gene (relevant to certain cancers), HIV, and other genetic characteristics.

Computer-aided techniques for monitoring gene expression using such arrays of probes have also been developed as disclosed in U.S. patent application Ser. No. 08/828,952 and PCT Publication No. WO 97/10365, the contents of which are herein incorporated by reference. Many disease states are characterized by differences in the expression levels of various genes either through changes in the copy number of the genetic DNA or through changes in levels of transcription (e.g., through control of initiation, provision of RNA precursors, RNA processing, etc.) of particular genes. For example, losses and gains of genetic material play an important role in malignant transformation and progression. Furthermore, changes in the expression (transcription) levels of particular genes (e.g., oncogenes or tumor suppressors), serve as signposts for the presence and progression of various cancers.

It is desirable to identify genes having expression levels relevant to diagnosis of a diseased state by analyzing the expression levels of large numbers of genes in both diseased and normal individuals. Methods for collecting the expression level information have been developed. However, the user interfaces for gene expression monitoring systems that have been developed until now are designed to clearly present the expression of particular pre-selected genes. A user seeking to identify, e.g., an oncogene or a tumor suppressor gene, must individually review the expression level of large numbers of genes and compare the expression levels between diseased and normal individuals. What is needed is a user interface that takes advantage of collected gene expression information to help the user to identify particular genes of interest.

SUMMARY OF THE INVENTION

The present invention provides innovative systems and methods for visualizing information collected from analyzing samples. The samples may include nucleic acids, proteins, or other polymers. Gene expression level as determined from analysis of a nucleic acid sample is one possible analysis result that may be visualized. In one embodiment, a computer system may display the expression levels of multiple genes simultaneously in a way that facilitates user identification of genes whose expression is significant to a characteristic such as disease or resistance to disease. Additionally, the computer system may facilitate display of further information about relevant genes once they are identified.

A first aspect of the invention provides a computer-implemented method for presenting expression level information as collected from first and second samples. The method includes steps of: displaying a first axis corresponding to expression level in the first sample, and displaying a second axis substantially perpendicular to the first axis, the second axis corresponding to expression level in the second sample. The method further includes a step of: for a selected expressed sequence, displaying a mark at a position. The position is selected relative to the first axis in accordance with an expression level of the selected expressed sequence in the first sample and relative to the second axis in accordance with an expression level of the selected expressed sequence in the second sample. A particularly useful application is displaying many marks simultaneously for many selected genes to discover which ones of the selected genes may be relevant to the characteristic.

A second aspect of the invention provides a computer-implemented method of presenting sample analysis information. The method includes steps of: displaying a first axis corresponding to a concentration of a compound in a first sample as determined by monitoring binding of the compound to a selected polymer having binding affinity to the compound, and displaying a second axis substantially perpendicular to the first axis. The second axis corresponds to a concentration of the compound in the second sample as determined by monitoring binding of the compound to the selected polymer. The method further preferably includes a step of displaying a mark at a position. The position is selected relative to the first axis in accordance with the concentration in the first sample and relative to the second axis in accordance with the concentration in the second sample.

A further understanding of the nature and advantages of the inventions herein may be realized by reference to the remaining portions of the specification and the attached drawings.

BRIEF DESCRIPTION OF THE DRAWINGS

FIG. 6 shows a screen display illustrating gene expression levels for multiple genes as collected from both normal and diseased tissue.

FIGS. 7A–7B show screen displays illustrating information (SEQ ID NOS: 1 and 2) about a particular gene from the display of FIG. 6.

DESCRIPTION OF SPECIFIC EMBODIMENTS

The present invention provides innovative methods of monitoring visualizing gene expression. In the description that follows, the invention will be described in reference to preferred embodiments. However, the description is provided for purposes of illustration and not for limiting the spirit and scope of the invention.

Figure 1:
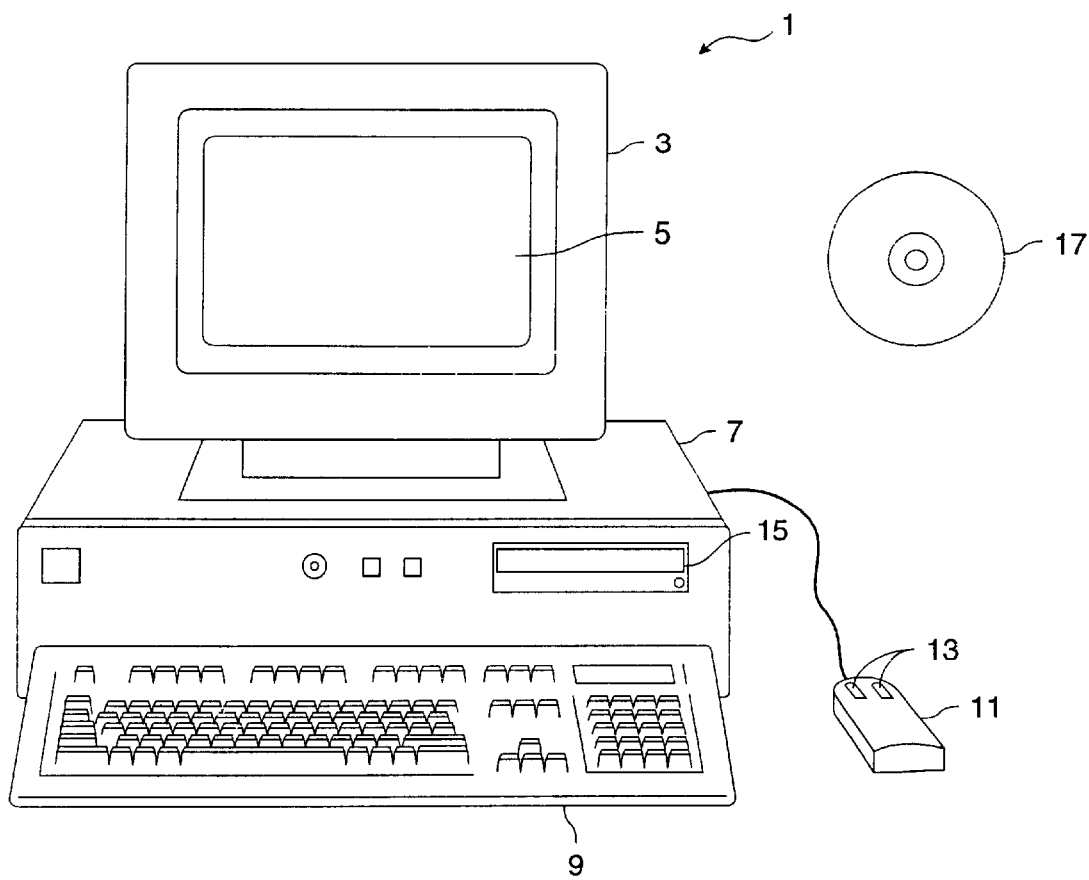
FIG. 1 illustrates an example of a computer system that may be used to execute software embodiments of the present invention.

FIG. 1 illustrates an example of a computer system that may be used to execute software embodiments of the present invention. FIG. 1 shows a computer system 1 which includes a monitor 3, screen 5, cabinet 7, keyboard 9, and mouse 11. Mouse 11 may have one or more buttons such as mouse buttons 13. Cabinet 7 houses a CD-ROM drive 15 and a hard drive (not shown) that may be utilized to store and retrieve software programs including computer code incorporating the present invention. Although a CD-ROM 17 is shown as the computer readable medium, other computer readable media including floppy disks, DRAM, hard drives, flash memory, tape, and the like may be utilized. Cabinet 7 also houses familiar computer components (not shown) such as a processor, memory, and the like.

Figure 2:
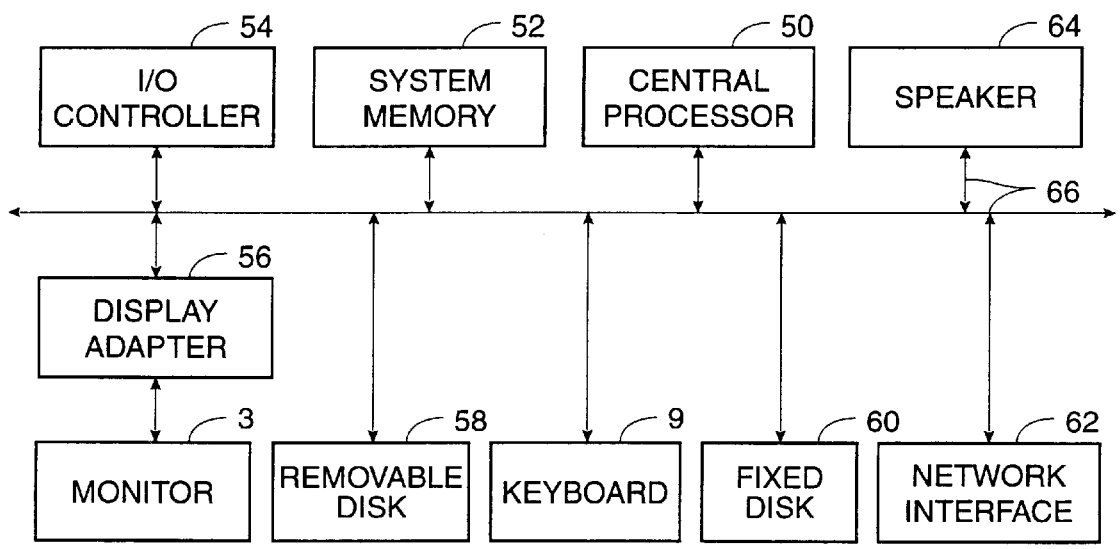
FIG. 2 shows a system block diagram of a typical computer system.

FIG. 2 shows a system block diagram of computer system 1 used to execute software embodiments of the present invention. As in FIG. 1, computer system 1 includes monitor 3 and keyboard 9. Computer system 1 further includes subsystems such as a central processor 50, system memory 52, I/O controller 54, display adapter 56, removable disk 58, fixed disk 60, network interface 62, and speaker 64. Removable disk 58 is representative of removable computer readable media like floppies, tape, CD-ROM, removable hard drive, flash memory, and the like. Fixed disk 60 is representative of an internal hard drive or the like. Other computer systems suitable for use with the present invention may include additional or fewer subsystems. For example, another computer system could include more than one processor 50 (i.e., a multi-processor system) or memory cache.

Arrows such as 66 represent the system bus architecture of computer system 1. However, these arrows are illustrative of any interconnection scheme serving to link the subsystems. For example, display adapter 56 may be connected to central processor 50 through a local bus or the system may include a memory cache. Computer system 1 shown in FIG. 2 is but an example of a computer system suitable for use with the present invention. Other configurations of subsystems suitable for use with the present invention will be readily apparent to one of ordinary skill in the art. In one embodiment, the computer system is an IBM compatible personal computer.

The VLSIPS™ and GeneChip™ technologies provide methods of making and using very large arrays of polymers, such as nucleic acids, on very small chips. See U.S. Pat. No. 5,143,854 and PCT Pat. Publication Nos. WO 90/15070 and 92/10092, each of which is hereby incorporated by reference for all purposes. Nucleic acid probes on the chip are used to detect complementary nucleic acid sequences in a sample nucleic acid of interest (the "target" nucleic acid).

It should be understood that the probes need not be nucleic acid probes but may also be other receptors, such as antibodies, or polymers such as peptides. Peptide probes may be used to detect the concentration of other peptides, proteins, or other compounds in a sample. The probes must be carefully selected to have bonding affinity to the compound whose concentration they are to be used to measure.

In one embodiment, the present invention provides methods of visualizing information relating to the concentration of compounds in a sample as measured by monitoring affinity of the compounds to probes. In a particular application, the concentration information is generated by analysis of hybridization intensity files for a chip containing hybridized nucleic acid probes. The hybridization of a nucleic acid sample to certain probes may represent the expression level of one more genes or expressed sequence tags (ESTs). The expression level of a gene or EST is herein understood to be the concentration within a sample of mRNA or protein that would result from the transcription of the gene or EST.

Expression level information visualized by virtue of the present invention need not be obtained from probes but may originate from any source. If the expression information is collected from a probe array, the probe array need not meet any particular criteria for size and density. Furthermore, the present invention is not limited to visualizing fluorescent measurements of bondings such as hybridizations but may be readily utilized to visualize other measurements.

Concentration of compounds other than nucleic acids may be visualized according to one embodiment of the present invention. For example, a probe array may include peptide probes which may be exposed to protein samples, polypeptide samples, or other compounds which may or may not bond to the peptide probes. By appropriate selection of the peptide probes, one may detect the presence or absence of particular compounds which would bond to the peptide probes.

For purposes of illustration, the present invention is described as being part of a system that designs a chip mask, synthesizes the probes on the chip, labels nucleic acids from a target sample, and scans the hybridized probes. Such a system is set forth in U.S. Pat. No. 5,571,639 which is hereby incorporated by reference for all purposes. However, the present invention may be used separately from the overall system for analyzing data generated by such systems, such as at remote locations, or for visualizing the results of other systems for generating expression information, or for visualizing concentrations of polymers other than nucleic acids.

Figure 3:
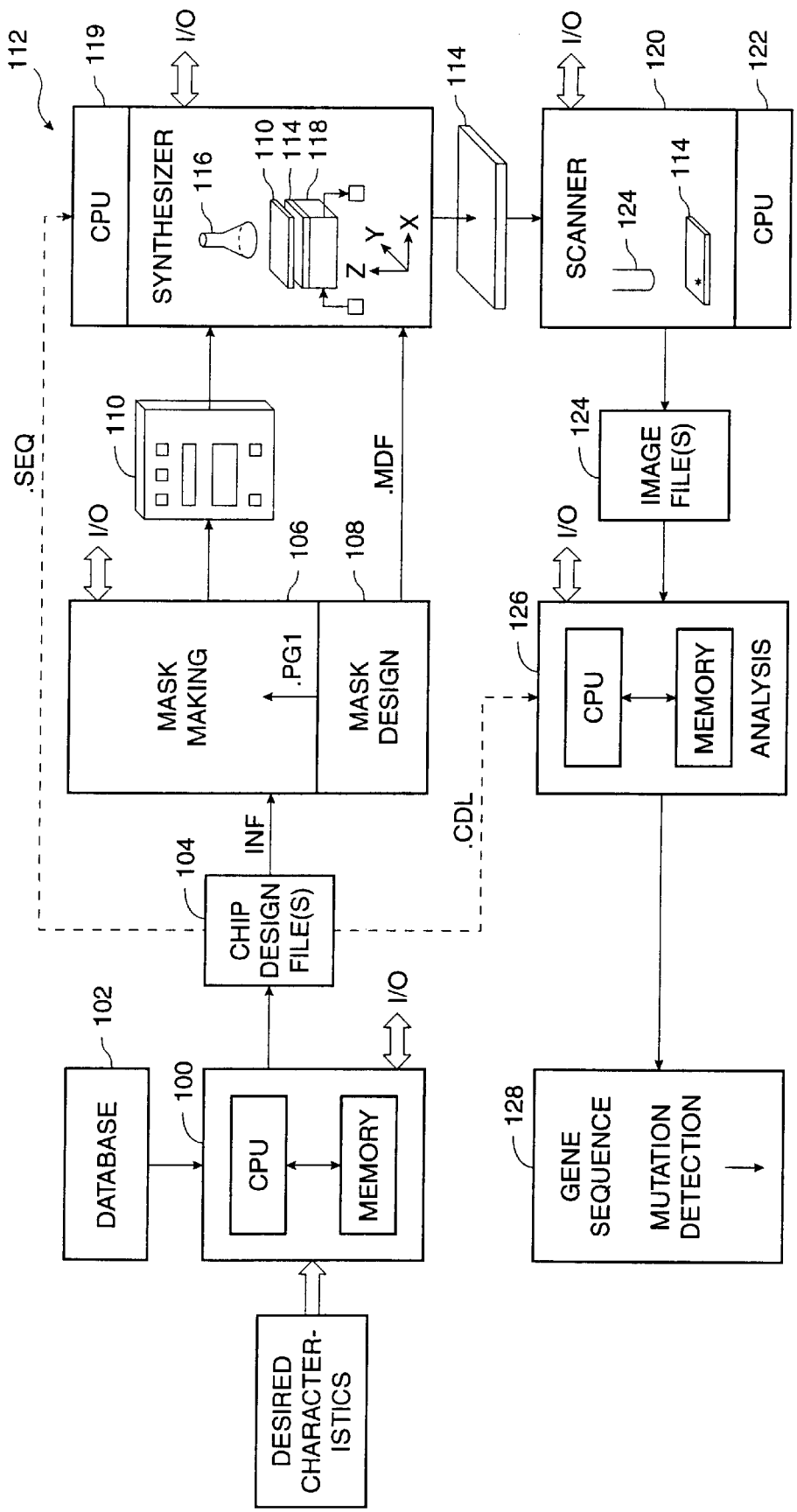
FIG. 3 illustrates an overall system for forming and analyzing arrays of polymers including biological materials such as DNA or RNA.

FIG. 3 illustrates a computerized system for forming and analyzing arrays of biological materials such as RNA or DNA. A computer 100 is used to design arrays of biological polymers such as RNA or DNA. The computer 100 may be, for example, an appropriately programmed IBM personal computer compatible running Windows NT including appropriate memory and a CPU as shown in FIGS. 1 and 2. The computer system 100 obtains inputs from a user regarding characteristics of a gene of interest, and other inputs regarding the desired features of the array. Optionally, the computer system may obtain information regarding a specific genetic sequence of interest from an external or internal database 102 such as GenBank. The output of the computer system 100 is a set of chip design computer files 104 in the form of, for example, a switch matrix, as described in PCT application WO 92/10092, and other associated computer files.

The chip design files are provided to a system 106 that designs the lithographic masks used in the fabrication of arrays of molecules such as DNA. The system or process 106 may include the hardware necessary to manufacture masks 110 and also the necessary computer hardware and software 108 necessary to lay the mask patterns out on the mask in an efficient manner. As with the other features in FIG. 3, such equipment may or may not be located at the same physical site, but is shown together for ease of illustration in FIG. 3. The system 106 generates masks 110 or other synthesis patterns such as chrome-on-glass masks for use in the fabrication of polymer arrays.

The masks 110, as well as selected information relating to the design of the chips from system 100, are used in a synthesis system 112. Synthesis system 112 includes the necessary hardware and software used to fabricate arrays of polymers on a substrate or chip 114. For example, synthesizer 112 includes a light source 116 and a chemical flow cell 118 on which the substrate or chip 114 is placed. Mask 110 is placed between the light source and the substrate/chip, and the two are translated relative to each other at appropriate times for deprotection of selected regions of the chip. Selected chemical reagents are directed through flow cell 118 for coupling to deprotected regions, as well as for washing and other operations. All operations are preferably directed by an appropriately programmed computer 119, which may or may not be the same computer as the computer(s) used in mask design and mask making.

The substrates fabricated by synthesis system 112 are optionally diced into smaller chips and exposed to marked targets. The targets may or may not be complementary to one or more of the molecules on the substrate. The targets are marked with a label such as a fluorescein label (indicated by an asterisk in FIG. 3) and placed in scanning system 120. Scanning system 120 again operates under the direction of an appropriately programmed digital computer 122, which also may or may not be the same computer as the computers used in synthesis, mask making, and mask design. The scanner 120 includes a detection device 124 such as a confocal microscope or CCD (charge-coupled device) that is used to detect the location where labeled target has bound to the substrate. The output of scanner 120 is an image file(s) 124 indicating, in the case of fluorescein labeled target, the fluorescence intensity (photon counts or other related measurements, such as voltage) as a function of position on the substrate. Since higher photon counts will be observed where the labeled target has bound more strongly to the array of polymers, and since the monomer sequence of the polymers on the substrate is known as a function of position, it becomes possible to determine the sequence(s) of polymer (s) on the substrate that are complementary to the target.

The image file 124 is provided as input to an analysis system 126 that incorporates the visualization and analysis methods of the present invention. Again, the analysis system may be any one of a wide variety of computer system. The present invention provides various methods of analyzing and visualizing the chip design files and the image files, providing appropriate output 128. The chip design need not include any particular number of probes. It should be understood that the present invention does not require any particular source of expression level information.

Figure 4:
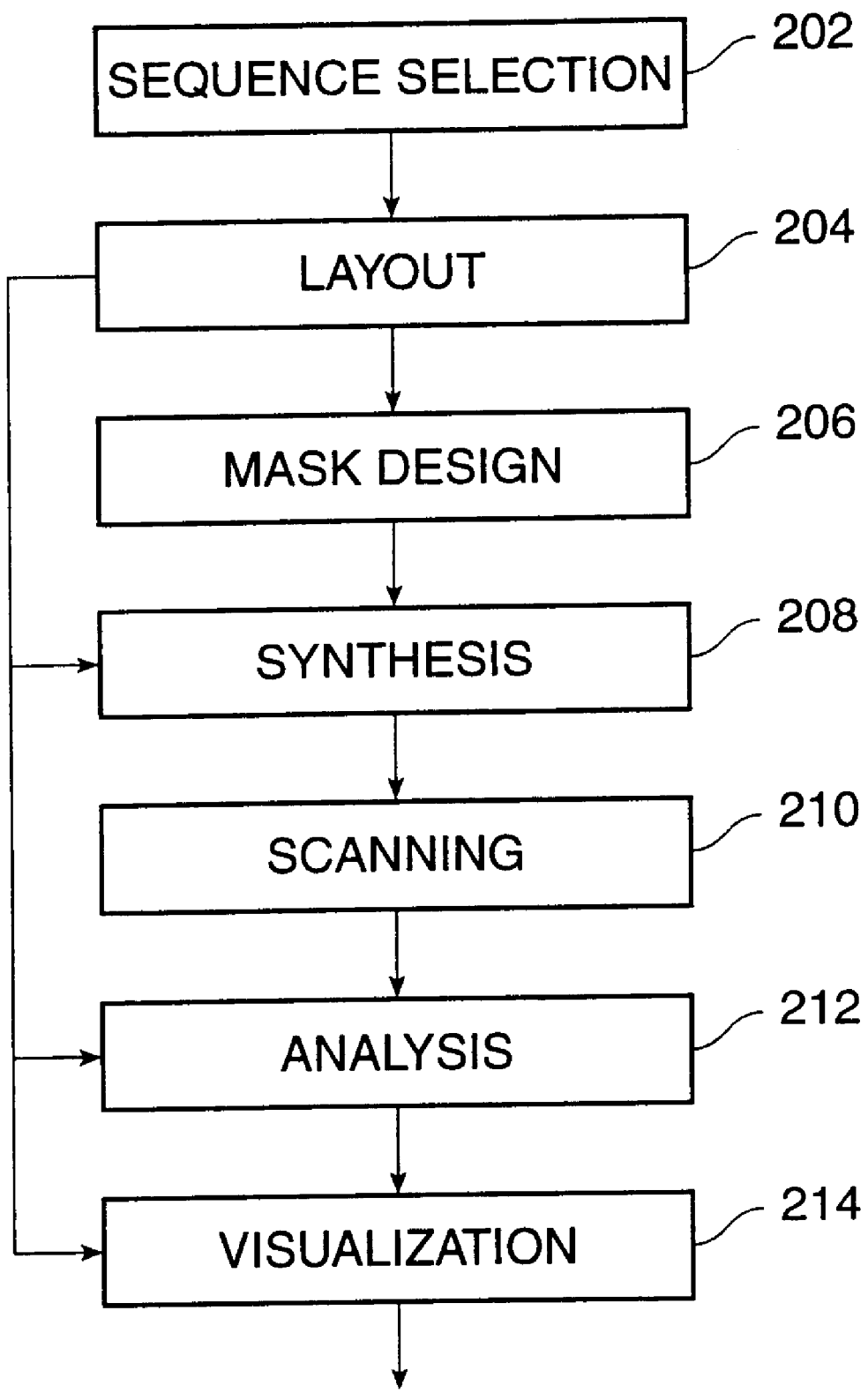
FIG. 4 is an illustration of an embodiment of software for the overall system.

FIG. 4 provides a simplified illustration of the overall software system used in the operation of one embodiment of the invention. As shown in FIG. 4, the system first identifies the nucleotide sequence(s) or targets that would be of interest in a particular expression level analysis at step 202. The sequences of interest correspond to mRNA transcripts of one or more genes, ESTs or nucleic acids derived from the mRNA transcripts. Sequence selection may be provided via manual input of text files or may be from external sources such as GenBank.

At step 204 the system evaluates the sequences of interest to determine or assist the user in determining which probes would be desirable on the chip, and provides an appropriate "layout" on the chip for the probes. The process of selecting probes for an expression level analysis is explained in PCT Publication No. WO 97/10365, the contents of which are herein incorporated by reference. An alternative probe selection process that does not require prior knowledge of sequences of interest is explained in PCT Publication No. WO97/27317, the contents of which are herein incorporated by reference. Further general background on probe selection is found in PCT Publication No. WO95/11995 and PCT Publication No. WO97/29212, the contents of which are herein incorporated by reference. The term "perfect match probe" refers to a probe that has a sequence that is perfectly complementary to a particular target sequence. The test probe is typically perfectly complementary to a portion (subsequence) of the target sequence. The term "mismatch control" or "mismatch probe" refer to probes whose sequence is deliberately selected not to be perfectly complementary to a particular target sequence. For each mismatch (MM) control in an array there typically exists a corresponding perfect match (PM) probe that is perfectly complementary to the same particular target sequence.

The process compares hybridization intensities of pairs of perfect match and mismatch probes that are preferably covalently attached to the surface of a substrate or chip. Most preferably, the nucleic acid probes have a density greater than about 60 different nucleic acid probes per 1 $cm^2$ of the substrate.

Initially, nucleic acid probes are selected that are complementary to the target sequence. These probes are the perfect match probes. Another set of probes is specified that are intended to be not perfectly complementary to the target sequence. These probes are the mismatch probes and each mismatch probe includes at least one nucleotide mismatch from a perfect match probe. Accordingly, a mismatch probe and the perfect match probe to which it is identical except for one base make up a pair. As mentioned earlier, the nucleotide mismatch is preferably near the center of the mismatch probe.

The probe lengths of the perfect match probes are typically chosen to exhibit detectably greater hybridization with the target sequence relative to the mismatch probes. For example, the nucleic acid probes may be all 20-mers. However, probes of varying lengths may also be synthesized on the substrate for any number of reasons including resolving ambiguities.

Again referring to FIG. 4, at step 206 the masks for the synthesis are designed. At step 208 the software utilizes the mask design and layout information to make the DNA or other polymer chips. This step 208 will control, among other things, relative translation of a substrate and the mask, the flow of desired reagents through a flow cell, the synthesis temperature of the flow cell, and other parameters. At step 210, another piece of software is used in scanning a chip thus synthesized and exposed to a labeled target. The software controls the scanning of the chip, and stores the data thus obtained in a file that may later be utilized to extract hybridization information.

At step 212 a computer system utilizes the layout information and the fluorescence information to evaluate the hybridized nucleic acid probes on the chip. Among the important pieces of information obtained from DNA chips are the relative fluorescent intensities obtained from the perfect match probes and mismatch probes. These intensity levels are used to estimate an expression level for a gene or EST. The computer system used for analysis will preferably have available other details of the experiment including possibly the gene name, gene sequence, probe sequences, probe locations on the substrate, and the like.

According to the present invention, at step 214, the same computer system used for analysis or another one displays the expression level information in a format useful for identifying genes of interest. The visualized expression level information may include information collected from multiple applications of one or more previous steps of FIG. 4.

Figure 5:
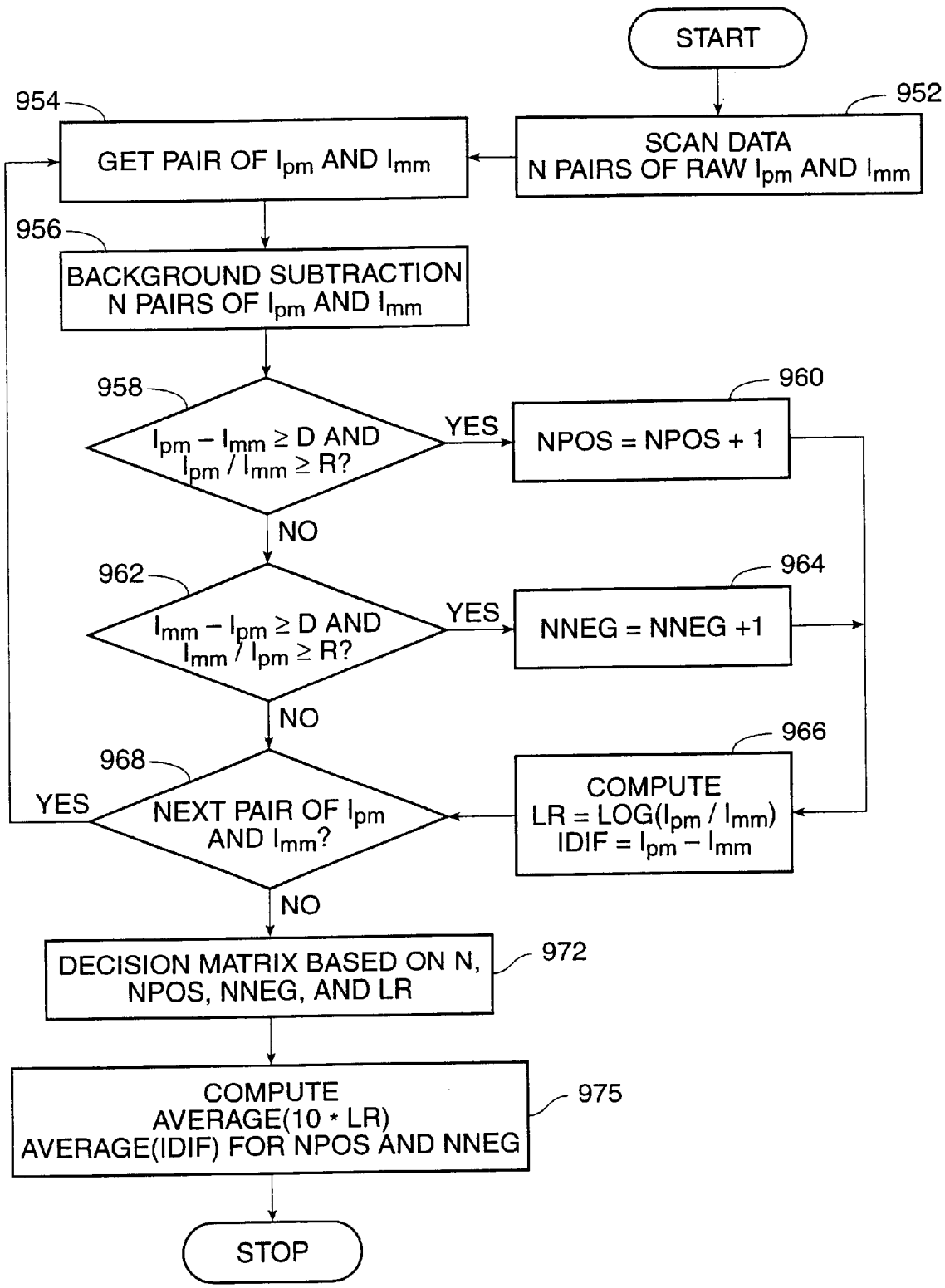
FIG. 5 shows a flowchart of a process of monitoring the expression of a gene by comparing hybridization intensities of pairs of perfect match and mismatch probes.

FIG. 5 is a flowchart describing steps of estimating an expression level for a particular gene and determining whether the expression level is sufficiently high to be displayed. At step 952, the computer system receives raw scan data of N pairs of perfect match and mismatch probes. In a preferred embodiment, the hybridization intensities are photon counts from a fluorescein labeled target that has hybridized to the probes on the substrate. For simplicity, the hybridization intensity of a perfect match probe will be designed "$I_{pm}$" and the hybridization intensity of a mismatch probe will be designed "$I_{mm}$."

Hybridization intensities for a pair of probes are retrieved at step 954. The background signal intensity is subtracted from each of the hybridization intensities of the pair at step 956. Background subtraction can also be performed on all the raw scan data at the same time.

At step 958, the hybridization intensities of the pair of probes are compared to a difference threshold (D) and a ratio threshold (R). It is determined if the difference between the hybridization intensities of the pair ($I_{pm}-I_{mm}$) is greater than or equal to the difference threshold AND the quotient of the hybridization intensities of the pair ($I_{pm}/I_{mm}$) is greater than or equal to the ratio threshold. The difference thresholds are typically user defined values that have been determined to produce accurate expression monitoring of a gene or genes. In one embodiment, the difference threshold is 20 and the ratio threshold is 1.2.

If $I_{pm}-I_{mm}>=D$ and $I_{pm}/I_{mm}>=R$, the value NPOS is incremented at step 960. In general, NPOS is a value that indicates the number of pairs of probes which have hybridization intensities indicating that the gene is likely expressed. NPOS is utilized in a determination of the expression of the gene.

At step 962, it is determined if $I_{mm}-I_{pm}>=D$ and $I_{mm}/I_{pm}>=R$. If these expressions are true, the value NNEG is incremented at step 964. In general, NNEG is a value that indicates the number of pairs of probes which have hybridization intensities indicating that the gene is likely not expressed. NNEG, like NPOS, is utilized in a determination of the expression of the gene.

For each pair that exhibits hybridization intensities either indicating the gene is expressed or not expressed, a log ratio value (LR) and intensity difference value (IDIF) are calculated at step 966. LR is calculated by the log of the quotient of the hybridization intensities of the pair ($I_{pm}/I_{mm}$). The IDIF is calculated by the difference between the hybridization intensities of the pair ($I_{pm}-I_{mm}$). If there is a next pair of hybridization intensities at step 968, they are retrieved at step 954.

At step 972, a decision matrix is utilized to indicate if the gene is expressed. The decision matrix utilizes the values N, NPOS, NNEG, LR (multiple LRs), and IDIF (multiple IDIFs). The following four assignments are performed:

P1=NPOS/NNEG
P2=NPOS/N
P3=SUM(LR)/N
P4=SUM(IDIF)/N

These P values are then utilized to determine if the gene is expressed and if the expression level should be displayed.

In a preferred embodiment, the expression level of a gene should be displayed if:

P1>2.2
P2>0.3
P3>0.8
P4>30

Once all the pairs of probes have been processed and the expression of the gene indicated, an average of the IDIF values for the probes that incremented NPOS or NNEG is calculated at step 975, which is utilized as an expression level. Of course, other values including one of P1 through P4 could be used to indicate expression level.

For simplicity, FIG. 5 was described in reference to a single gene or EST. However, the visualization system of the present invention displays expression results for many genes to facilitate discovery of genes of interest or ESTs. Furthermore, the present invention contemplates display of expression levels of a single gene or ESTs as collected from two or more different samples such as tissue samples. The sample sources preferably differ in some characteristic. It will be understood that when the term "sample" is used herein, measurements made on a single "sample" can be based on an aggregation of multiple sample collection events or even multiple organisms.

Figures 6, 7A:
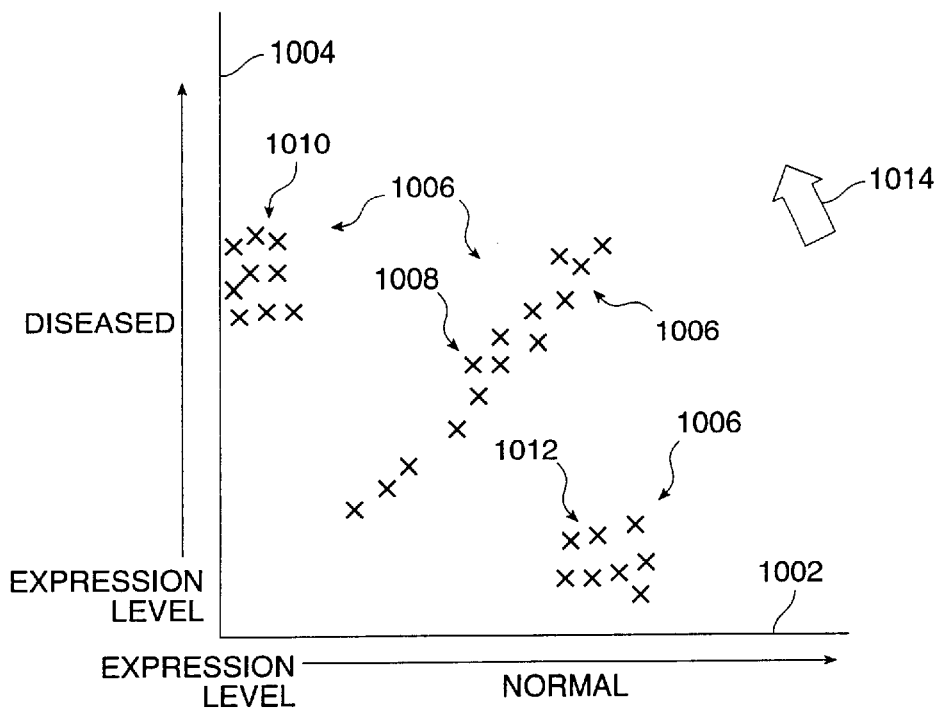

FIG. 6 shows a screen display illustrating gene expression levels for multiple genes as collected from two tissue samples. A displayed horizontal axis 1002 represents expression level measured in one or more nucleic acid samples taken from the first tissue sample. A displayed vertical axis 1004 represents expression level in one or more nucleic acid samples taken from the second tissue sample. Each of marks 1006 represent a particular gene whose expression level has been measured in both the first and second tissue samples. Each mark 1006 is placed at a distance from vertical axis 1004 corresponding to expression level in the first tissue sample and at a distance from the horizontal axis 1002 corresponding to expression level in the second tissue sample.

The expression levels used for determining the position of marks 1006 are preferably taken from the result of step 975. The position of each of marks 1006 depends on two iterations of the steps of FIG. 5, once for the sample taken from the first tissue sample and once for the sample taken from the second tissue sample. However, a mark is preferably displayed only if one of the samples meets the threshold criteria at step 972.

In the depicted representative screen display, the first tissue sample is a cancerous tissue sample and the second tissue sample is a normal tissue sample. The individual marks represent the expression levels of selected genes in both cancerous and normal tissue. A first group of marks 1008 represent genes that are neither tumor suppressors nor oncogenes since their expression levels are roughly similar for both normal and cancerous tissue. These marks 1008 fall roughly along a line which is rotated 45 degrees from each of the axes. A second group of marks 1010 represent genes that are likely oncogenes since their expression levels are found to be significantly higher in cancerous tissue than in normal tissue. A third group of marks 1012 represent genes that are likely tumor suppressors since their expression levels are found to be significantly higher in normal tissue than in cancerous tissue. It will be appreciated that expression levels for large numbers of genes can be reviewed at once to discover the oncogenes and tumor suppressors.

Although in the depicted display, the two types of tissue are normal tissue and cancerous tissue, the present invention would aid in the discovery of genes whose expression is associated with any characteristic that varies among tissue samples. For example, one can compare expression results from tissue from individuals who have been exposed to HIV but remain infected to tissue obtained from infected individuals to identify genes conferring resistance to HIV. One can compare expression results between tissue from plants that survive drought to plants that do not. One can compare expression levels among tissue samples at successive stages or severity levels of the same disease, among tissue samples where different ultimate outcomes of the disease (e.g., patient death or remission) are known, among diseased tissue samples that have been subject to different treatment regimes including e.g, chemotherapy, antisense RNA, etc. For cancers one can compare expression levels between malignant cells and non-malignant cells. Also expression levels can be compared among different organs, between species, and among different stages of development of an organ.

It will be appreciated that the present invention also encompasses displays with more than two dimensions. A third visual dimension can be used to illustrate expression level from a third tissue sample. The time dimension can also be used to illustrate successive groups of two or three tissue samples at successive time periods. The time dimension can be also used to correspond to tissue samples obtained at, e.g, successive stages of a disease.

Other interface methods corresponding to human senses other than sight can also be incorporated within the presentation system of the present invention. The senses may correspond to additional dimensions. For example, marks can be displayed in succession accompanies by a sound having characteristics corresponding to expression level in another tissue sample.

The user can employ a cursor 1014 to identify a particular mark as being of interest. Cursor 1014 can be moved to a particular mark by use of, e.g., mouse 11. Once cursor 1014 is over a mark of interest, the mark can be selected by, e.g., depression of one of mouse buttons 13. Selection of a particular mark can be facilitated by use of a zoom display feature (not shown). Once a particular mark is selected, further information is displayed about the gene represented by the mark. A special mouse can transmit a tactile sensation back to the user corresponding to expression level in a tissue sample as the user passes the mouse over a corresponding mark.

It will be appreciated that the display of FIG. 6 is not limited to expression information. The two dimensions of FIG. 6 may correspond to indicators of the presence of various polymers other than nucleic acids in two different samples. For example, each mark may correspond to a different polymer, polypeptide, or other compound. The distance of the mark from each axis would correspond to a measure of presence of the particular polymer in the sample corresponding to the axis. One possible measure is produced by fluorescently tagging polymer samples such as protein samples and exposing a probe array such as a peptide probe array to the protein samples. The fluorescent intensity of the probes will then correspond to the bonding affinity of the sample to the probes. The intensity measurement or a measurement derived from the intensity measurement may then be used to position the marks of FIG. 6.

FIG. 7A shows a screen display giving information about a particular gene selected from the display of FIG. 6. A cluster number 702, a GenBank accession number 704, and a verbal description 706 for the selected gene are displayed. The user can also select a number of marks 1006 by circling them with cursor 1014. Then a list of information as shown in FIG. 7A is displayed for all the genes corresponding to the selected marks.

By selecting GenBank accession number 704 with another cursor (not shown), the user can direct retrieval of the GenBank information for the selected gene. If the GenBank information is not available locally, the retrieval process can include formulating a query and transmitting the query to a GenBank web site. Once the GenBank information is retrieved, it can also be displayed. FIG. 7B depicts the GenBank information for the gene identified in FIG. 7A.

In the foregoing specification, the invention has been described with reference to specific exemplary embodiments thereof. It will, however, be evident that various modifications and changes may be made thereunto without departing from the broader spirit and scope of the invention as set forth in the appended claims and their full scope of equivalents.

What is claimed is:

1. A computer-implemented method of presenting expression level information as collected from first and second samples, said method comprising:

displaying a first axis indicating expression level in said first sample;

displaying a second axis substantially perpendicular to said first axis, said second axis indicating expression level in said second sample; for a selected expressed sequence, displaying a mark at a position with an X coordinate and a Y coordinate, wherein the X coordinate of said position is selected relative to said first axis and said Y coordinate of said position is selected relative to said second axis, wherein said position is selected relative to said first axis in accordance with an expression level of said selected expressed sequence in said first sample and relative to said second axis in accordance with an expression level of said selected expressed sequence in said second sample;

receiving an input of a user's selection of said mark; and in response to said user input, displaying information about said selected expressed sequence.

2. The method of claim 1 wherein said selected expressed sequence comprises a gene.

3. The method of claim 1 wherein said selected expressed sequence comprises a portion of a gene.

4. The method of claim 1 further comprising;

repeatedly displaying a mark for each one of a plurality of selected expressed sequences.

5. The method of claim 1 further comprising:

monitoring said expression level of said expressed sequence in said first sample and said second sample.

6. The method of claim wherein said monitoring further comprises inputting a plurality of hybridization intensities from pairs of perfect match and mismatch probes, said perfect match probes being perfectly complementary to a target nucleic acid sequence indicative of expression of said selected gene and said mismatch probes having at least one base mismatch with said target sequence, and said hybridization intensities indicating hybridization affinity between said perfect match and mismatch probes and a sample nucleic acid sequence from said one of said samples;

comparing the hybridization intensities of each pair of perfect match probe and mismatch probe; and generating said expression level for said expressed sequence and said one of said samples responsive to results of said comparing.

7. The method of claim 6 further comprising comparing a difference between hybridization intensities of perfect match and mismatch probes at a base position to a difference threshold.

8. The method of claim 7 further comprising:

comparing a quotient of hybridization intensities of perfect match and mismatch probes at a base position to a ratio threshold.

9. The method of claim 6 further comprising:

a) counting a probe pair as a positive probe pair to increment a positive probe pair count if a perfect match probe intensity minus a mismatch probe intensity exceeds a difference threshold and said perfect match probe intensity divided by said mismatch probe intensity exceeds a ratio threshold;

b) counting said probe pair as a negative probe pair to increment a negative probe pair count if said mismatch probe intensity minus said perfect match probe intensity exceeds said difference threshold and said mismatch probe intensity divided by said perfect match probe intensity exceeds said ratio threshold;

c) computing a logarithmic ratio of said perfect match probe intensity to said mismatch probe intensity; and d) computing a difference of said perfect match probe intensity to said mismatch probe intensity.

10. The method of claim 9 further comprising:

repeating said a), b), c) and d) steps for each of said probe pairs, accumulating a sum of differences of said perfect match and mismatch probe intensities for probe pairs that exhibit said difference; and determining an expression level of said selected expressed sequence to be an average of said differences.

11. The method of claim 11 further comprising:

in response to said input, displaying information about said selected expressed sequence; said information comprising an identifier for said selected expressed sequence.

12. The method of claim 11 wherein said identifier for said selected expressed sequence comprises a GenBank accession number.

13. The method of claim 11 wherein said information about said selected expressed sequence comprises a GenBank database record for said selected expressed sequence.

14. The method of claim 1 wherein said first sample and said second sample are collected from tissue samples differing in a particular characteristic.

15. The method of claim 14 wherein said particular characteristic comprises a disease state.

16. The method of claim 14 wherein said particular characteristic comprises a treatment strategy for a disease.

17. The method of claim 1 wherein said particular characteristic is a stage of a disease.

18. The method of claim 1 further comprising:
displaying a third axis substantially perpendicular to said first axis and to said second axis in a three-dimensional display environment wherein said position of said mark is further selected relative to said third axis in accordance with an expression level of said selected expressed sequence in a third sample.

19. A computer-implemented method of presenting sample analysis information comprising:
displaying a first axis indicating a concentration of a compound in a first sample as determined by monitoring binding of said compound to a selected polymer having binding affinity to said compound;
displaying a second axis substantially perpendicular to said first axis, said second axis indicating a concentration of said compound in said second sample as determined by monitoring binding of said compound to said selected polymer; and
displaying a mark at a position with an X coordinate and a Y coordinate, wherein the X coordinate of said position is selected relative to said first axis and said Y coordinate of said position is selected relative to said second axis, wherein said position is selected relative to said first axis in accordance with said concentration in said first sample and relative to said second axis in accordance with said concentration in said second samples;
receiving an input of a user's selection of said mark; and
in response to said user input displaying information about said compound.

20. The method of claim 19 wherein said selected polymer comprises a nucleic acid sequence.

21. The method of claim 19 wherein said selected polymer comprises a protein.

22. The method of claim 20 further comprising:
obtaining said concentration of said compound in said first sample by exposing said first sample to a plurality of nucleic acid probes.

23. The method of claim 21 further comprising:
obtaining said concentration of said compound in said first sample by exposing said first sample to a plurality of peptide probes.

24. A computer program product for presenting expression level information as collected from a first sample and a second sample, said product comprising:
code for displaying a first axis indicating expression level in said first sample;
code for displaying a second axis substantially perpendicular to said first axis, said second axis indicating expression level in said second sample;
code for, for a selected expressed sequence, displaying a mark at a position with an X coordinate and a Y coordinate wherein the X coordinate of said position is selected relative to said first axis and said Y coordinate of said position is selected relative to said second axis, wherein said position is selected relative to said first axis in accordance with an expression level of said selected expressed sequence in said first sample and relative to said second axis in accordance with an expression level of said selected expressed sequence in said second sample;
code for receiving an input from a user's selection of said mark;

code for displaying information about said selected expressed sequence in response to said user input; and
a computer-readable storage medium for storing the codes.

25. The product of claim 24 wherein said selected expressed sequence comprises a gene.

26. The product of claim 24 wherein said selected expressed sequence comprises a portion of a gene.

27. The product of claim 24 further comprising code for repeatedly applying said displaying a mark code for a plurality of selected expressed sequences.

28. The product of claim 24 further comprising:
code for monitoring said expression level of said expressed sequence in said first sample and said second sample.

29. The product of claim 28 wherein said code for monitoring for one of said samples comprises:
code for inputting a plurality of hybridization intensities from pairs of perfect match and mismatch probes, said perfect match probes being perfectly complementary to a target nucleic acid sequence indicative of expression of said selected gene and said mismatch probes having at least one base mismatch with said target sequence, and said hybridization intensities indicating hybridization affinity between said perfect match and mismatch probes and a sample nucleic acid sequence from said one of said samples;
code for comparing the hybridization intensities of each pair of perfect match probe and mismatch probe; and
code for generating said expression level for said expressed sequence and said one of said samples responsive to a result produced by said code for comparing.

30. The product of claim 29 further comprising:
code for comparing a difference between hybridization intensities of perfect match and mismatch probes at a base position to a difference threshold.

31. The product of claim 30 further comprising:
code for comparing a quotient of hybridization intensities of perfect match and mismatch probes at a base position to a ratio threshold.

32. The product of claim 29 further comprising:
a) code for counting a probe pair as a positive probe pair to increment a positive probe pair count if a perfect match probe intensity minus a mismatch probe intensity exceeds a difference threshold and said perfect match probe intensity divided by said mismatch probe intensity exceeds a ratio threshold;
b) code for counting said probe pair as a negative probe pair to increment a negative probe pair count if said mismatch probe intensity minus said perfect match probe intensity exceeds said difference threshold and said mismatch probe intensity divided by said perfect match probe intensity exceeds said ratio threshold; and
c) code for computing a logarithmic ratio of said perfect match probe to intensity to said mismatch probe intensity.

33. The product of claim 32 further comprising:
code for repeatedly applying said a), b), and c) codes for each of said probe pairs, accumulating a sum of differences of said perfect match and mismatch probe intensities for probe pairs that exhibit said difference; and
code for determining an expression level of said selected expressed sequence to be an average of said differences.

34. The product of claim 24 further comprising:

code for, in response to said input, displaying information about said selected expressed sequence; said information comprising an identifier for said selected expressed sequence.

35. The product of claim 34 wherein said identifier for said selected expressed sequence comprises a GenBank accession number.

36. The product of claim 34 wherein said information about said selected expressed sequence comprises a GenBank database record for said selected expressed sequence.

37. The product of claim 24 wherein said first sample and said second sample are collected from tissue samples differing in a particular characteristic.

38. The product of claim 37 wherein said particular characteristic comprises a disease state.

39. The product of claim 37 wherein said particular characteristic comprises a treatment strategy for a disease.

40. The product of claim 37 wherein said particular characteristic is a stage of a disease.

41. The product of claim 24 further comprising:

code for displaying a third axis substantially perpendicular to said first axis and to said second axis in a three-dimensional display environment wherein said position of said mark is further selected relative to said third axis in accordance with an expression level of said selected expressed sequence in a third sample.

42. A computer program product for presenting sample analysis information comprising:

code for displaying a first axis indicating a concentration of a compound in a first sample as determined by monitoring binding of said compound to a selected polymer having bonding affinity to said compound;

code for displaying a second axis substantially perpendicular to said first axis, said second axis indicating a concentration of said compound in a second sample as determined by monitoring binding of said compound to said selected polymer;

code for displaying a mark at a position with an X coordinate and a Y coordinate wherein the X coordinate of said position is selected relative to said first axis and said Y coordinate of said position is selected relative to said second axis, wherein said position is selected relative to said first axis in accordance with said concentration in said first sample and relative to said second axis in accordance with said concentration in said second sample;

code for receiving an input of a user's selection of said mark;

code for displaying information about said compound in response to said user input; and a computer-readable storage medium that stores the codes.

43. The product of claim 42 wherein said selected polymer comprises a nucleic acid sequence.

44. The product of claim 42 wherein said selected polymer comprises a protein.

45. A computer system comprising a display, a processor, and a memory that stores instructions for configuring said processor to:

display a first axis indicating expression level in said first sample;

display a second axis substantially perpendicular to said first axis, said second axis indicating expression level in said second sample; and for a selected expressed sequence, display a mark at a position with an X coordinate and a Y coordinate, wherein the X coordinate of said position is selected relative to said first axis and said Y coordinate of said position is selected relative to said second axis, wherein said position is selected relative to said first axis in accordance with an expression level of said selected expressed sequence in said first sample and relative to said second axis in accordance with an expression level of said selected expressed sequence in said second sample; wherein information about said selected expressed sequence is displayed responsive to an input of a user's selection of said mark.

46. A computer system comprising a display, a processor, and a memory that stores instructions for configuring said processor to:

display a first axis indicating a concentration of a compound in a first sample as determined by monitoring binding of said compound to a selected polymer having binding affinity to said compound;

display a second axis substantially perpendicular to said first axis, said second axis indicating a concentration of said compound in said second sample as determined by monitoring binding of said compound to said selected polymer; and display a mark at a position with an X coordinate and a Y coordinate, wherein the X coordinate of said position is selected relative to said first axis and said Y coordinate of said position is selected relative to said second axis, wherein said position is selected relative to said first axis in accordance with said concentration in said first sample and relative to said second axis in accordance with said concentration in said second sample; wherein information about said selected expressed sequence is displayed responsive to an input of a user's selection of said mark.

47. The method of claim 1 further comprising:

providing a tactile feedback to said user through a pointing device when a cursor is moved over said mark; said tactile feedback indicating expression level for said selected expressed sequence corresponding to said mark.

48. The method of claim 1 further comprising:

providing an aural indication to said user through a pointing device when a cursor is moved over said mark; said aural indication indicating expression level for said selected expressed sequence corresponding to said mark.

49. The method of claim 1 further comprising:

obtaining information from an internet based resource about a selected expressed sequence corresponding to said mark.

50. The method of claim 1 further comprising:

receiving from the user a selection of at least two of a plurality of marks, said marks;

displaying information about genes corresponding to said selection of at least two of a plurality of marks.

* * * * *

UNITED STATES PATENT AND TRADEMARK OFFICE
CERTIFICATE OF CORRECTION

PATENT NO. : 6,420,108 B2
APPLICATION NO. : 09/020743
DATED : July 16, 2002
INVENTOR(S) : Mack et al.

It is certified that error appears in the above-identified patent and that said Letters Patent is hereby corrected as shown below:

Column 15, line 50, claim 6 should read:

6. The method of claim 5, wherein said monitoring further comprises inputting a plurality of hybridization intensities from pairs of perfect match and mismatch probes, said perfect match probes being perfectly complementary to a target nucleic acid sequence indicative of expression of said selected gene and said mismatch probes having at least one base mismatch with said target sequence, and said hybridization intensities indicating hybridization affinity between said perfect match and mismatch probes and a sample nucleic acid sequence from said one of said samples; comparing the hybridization intensities of each pair of perfect match probe and mismatch probe; and generating said expression level for said expressed sequence and said one of said samples responsive to results of said comparing.

Signed and Sealed this

Seventeenth Day of October, 2006

JON W. DUDAS
*Director of the United States Patent and Trademark Office*